United States Patent [19]

Oroskar et al.

[11] Patent Number: 5,177,295
[45] Date of Patent: Jan. 5, 1993

[54] PROCESS FOR SEPARATING PARA-XYLENE FROM A $C_8$ AND $C_9$ AROMATIC MIXTURE

[75] Inventors: Anil R. Oroskar, Downers Grove; Roberto E. Prada, Mount Prospect; James A. Johnson; Gary C. Anderson, both of Clarendon Hills, all of Ill.; Hermann A. Zinnen, Summit, N.J.

[73] Assignee: UOP, Des Plaines, Ill.

[21] Appl. No.: 812,262

[22] Filed: Dec. 23, 1991

[51] Int. Cl.$^5$ .................... C07C 7/00; C07C 7/12
[52] U.S. Cl. ........................... 585/805; 585/828
[58] Field of Search .............. 585/805-828; 208/310 R

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,422,848 | 1/1969 | Liebman et al. | 137/625.15 |
| 3,686,342 | 8/1972 | Neuzil | 260/674 SA |
| 3,706,812 | 12/1972 | De Rosset et al. | 260/674 SA |
| 3,773,846 | 11/1973 | Beiger | 585/828 |
| 3,894,108 | 7/1975 | Geissler | 585/828 |
| 4,159,284 | 6/1979 | Seko et al. | 585/478 |
| 4,381,419 | 4/1983 | Wylie | 585/828 |
| 4,402,832 | 9/1983 | Gerhold | 210/659 |
| 4,478,721 | 10/1984 | Gerhold | 210/659 |
| 4,642,397 | 2/1987 | Zinnen et al. | 568/934 |
| 4,864,069 | 9/1989 | Zinnen | 585/828 |
| 4,886,930 | 12/1989 | Zinnen | 585/828 |
| 5,012,038 | 4/1991 | Zinnen | 585/828 |
| 5,057,643 | 10/1991 | Zinnen | 585/828 |

Primary Examiner—Anthony McFarlane
Assistant Examiner—Nhat Phan
Attorney, Agent, or Firm—Thomas K. McBride; John F. Spears, Jr.; Jack H. Hall

[57] ABSTRACT

In the process flow scheme for chromatographically separating para-xylene from $C_8$ isomers containing substantial amounts of $C_9$ aromatic hydrocarbon impurities with BaX or KY zeolite adsorbent and heavy desorbents, e.g., tetralin and diethyltoluene, a bottoms stream from the extract fractionation column containing desorbent is recycled to the separation unit and a sidecut stream, containing $C_9$ aromatic hydrocarbon impurities and a minor amount of the desorbent from the raffinate stream, is directed to the raffinate fractionation column, thereby removing $C_9$ aromatic hydrocarbons from the desorbent before recycling the desorbent to the separation unit, and preventing $C_9$ aromatics from building up in the desorbent input. A fractionator for the extract column bottoms stream is eliminated, lowering capital costs, and energy requirements for the raffinate column are reduced.

9 Claims, 1 Drawing Sheet

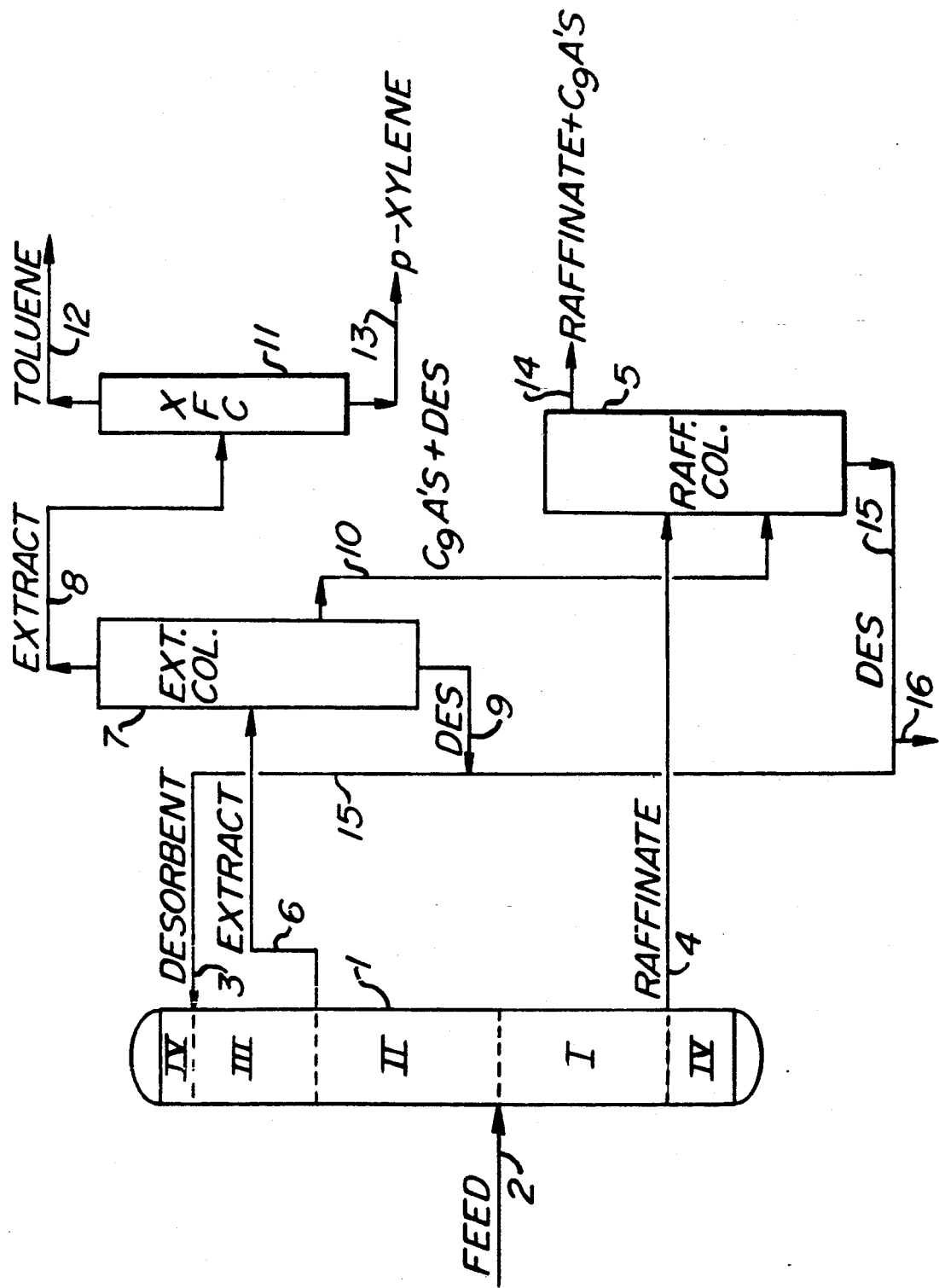

PROCESS FOR SEPARATING PARA-XYLENE FROM A C$_8$ AND C$_9$ AROMATIC MIXTURE

FIELD OF THE INVENTION

The present invention pertains to a process for the separation and recovery of para-xylene from a mixture of xylene isomers, including ethylbenzene, and especially those containing additional amounts of impurities in the form of C$_9$, C$_{10}$, etc., aromatic hydrocarbons. In particular, the process pertains to an adsorptive separation utilizing molecular sieve adsorbents to obtain para-xylene in relatively pure state from a mixture of xylene isomers and aromatic hydrocarbon impurities.

BACKGROUND OF THE INVENTION

In numerous processes described in the patent literature, X and Y zeolitic adsorbents exchanged with various cations are used with certain desorbents to separate the para-isomer of dialkyl-substituted monocyclic aromatics from the other isomers, particularly para-xylene from other xylene isomers. For example, in Neuzil et al U.S. Pat. No. 3,686,342, para-diethylbenzene is the preferred desorbent. More recently, in Zinnen U.S. Pat. Nos. 4,886,930; 4,864,069; 5,012,038 and U.S. Pat. No. 5,057,643, other "heavy" desorbents, e.g., diethyltoluene and tetralin and tetralin derivatives, have been disclosed for a process for separating para-xylene where the feed mixtures contain higher boiling aromatic hydrocarbons such as C$_9$ aromatics, C$_{10}$ aromatics, etc. With these C$_9$ and higher aromatic impurities in the feed, it is difficult to separate the desorbent, p-DEB, from the C$_9^+$ aromatics by fractionation because the boiling points of these materials are so close. If not removed, the C$_9$ aromatics would gradually build up in the desorbent, which must be recycled to the separation process for economic reasons.

U.S. Pat. No. 4,864,069 to Zinnen discloses a process for separating para-xylene from a mixture of xylene isomers with diethyltoluene as a heavy desorbent in which the heavy desorbent is recovered and recycled to the process by fractionating the raffinate to separate the desorbent from the xylene isomers and C$_9$ impurities. Likewise, after the para-xylene is removed from the extract in the extract column, the bottoms of the extract column (fractionation) contain desorbent and C$_9$ aromatic impurities which is further fractionated to recover the desorbent for return to the adsorbent separation process. In a co-pending application, Ser. No. 791,697, filed Nov. 14, 1991 the step of fractionating the extract bottoms to remove C$_9$ aromatic impurities from the desorbent recycle stream was eliminated by removing a portion of the extract bottoms stream and diverting the portion to the raffinate fractionation column where C$_9$ aromatics in the extract bottoms stream are separated from the desorbent, which is recycled to the separation step. In the present invention, the amount of desorbent in the C$_9$ aromatics sent to the raffinate column from the extract column is reduced, thereby lowering the energy input to the raffinate column and also reducing the raffinate column size and cost.

In U.S. Pat. Nos. 4,886,930 and 5,057,643 to Zinnen, a heavy desorbent, tetralin and derivatives, were disclosed for use in the separation of para-xylene from mixtures of xylene isomers. The recovery of the heavy desorbent from raffinate and extract streams by simple fractionation is also contemplated there.

It is also known that crystalline aluminosilicates, i.e., or zeolites, are used in adsorption separations of various mixtures in the form of agglomerates having high physical strength and attrition resistance. Methods for forming the crystalline powders into such agglomerates include the addition of an inorganic binder, generally a clay comprising a silicon dioxide and aluminum oxide, to the high purity zeolite powder in wet mixture. The blended clay zeolite mixture is extruded into cylindrical type pellets or formed into beads which are subsequently calcined in order to convert the clay to an amorphous binder of considerable mechanical strength. As binders, clays of the kaolin type, water permeable organic polymers or silica are generally used.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRosset U.S. Pat. No. 3,706,812) to commercial scale in flow rates from a few cc per hour to many thousands of gallons per hour.

The invention may also be practiced in a cocurrent, pulsed batch process, like that described in U.S. Pat. No. 4,159,284 or in a cocurrent, pulsed continuous process, like that disclosed in Gerhold U.S. Pat. Nos. 4,402,832 and 4,478,721.

The functions and properties of adsorbent and desorbents in the chromatographic separation of liquid components are well-known, but for reference thereto, Zinnen et al U.S. Pat. No. 4,642,397 is incorporated herein.

We have discovered a process for separating para-xylene from its isomers including ethylbenzene employing a zeolite adsorbent and a heavy desorbent whereby substantial economies can be obtained by the reduction of the quantity of desorbent required to be processed in the raffinate fractionation column. In this process, a sidecut stream comprising all of the C$_9$ aromatics in the extract is taken from the extract fractionation column. The sidecut stream contains from 10 to 20 percent of the desorbent charged to the extract column and is directed to the raffinate fractionation column to recover the desorbent. Since the sidecut removes all C$_9$ aromatics from the extract stream, C$_9$ aromatics are eliminated from the extract bottoms desorbent recycle stream.

SUMMARY OF THE INVENTION

In brief summary, the invention is a chromatographic process for separating p-xylene from a feed mixture comprising p-xylene and one or more additional xylene isomers (including ethylbenzene) and C$_9$ aromatic hydrocarbons comprising contacting the feed mixture with a zeolite adsorbent capable of effecting the selective adsorption of the p-xylene, removing a raffinate stream comprising the less selectively-adsorbed feed components and desorbent from contact with the adsorbent, contacting the adsorbent with a desorbent having a higher boiling point than the C$_9$ aromatic hydrocarbons, comprising diethyltoluene, tetralin or alkyl derivatives of tetralin, mixtures thereof or mixtures thereof with a normal paraffin, at desorption conditions, to effect the removal of an extract stream comprising C$_9$ aromatic hydrocarbons, para-xylene and desorbent, fractionating the extract stream in an extract fractionator to produce an extract overhead stream comprising para-xylene, a sidecut stream comprising substantially all the $C_9$ aromatics in the extract and a minor amount of the desorbent in the extract stream and an extract bottoms stream comprising a major amount of the desorbent from the extract stream, directing the sidecut stream to the raffinate column and fractionating the raffinate stream and the sidecut stream in a raffinate fractionator to produce a raffinate overhead stream comprising the less selectively adsorbed $C_8$ isomers and $C_9$ aromatics and a raffinate bottoms stream comprising desorbent. The raffinate and extract bottoms streams are recycled to the separation zone. By removing a sidecut stream from the extract fractionator and introducing it into the raffinate fractionator, $C_9$ aromatics are eliminated from the desorbent recycle stream and only a minor amount of desorbent from the extract stream must be processed in the raffinate column, thereby reducing overall energy requirements.

BRIEF DESCRIPTION OF THE DRAWING

The FIGURE is a flow scheme representing the process for separating para-xylene chromatographically from its isomers and $C_9$ aromatic hydrocarbons in which a sidecut stream containing minor amounts of desorbent and all the $C_9$ aromatic hydrocarbons in the extract is taken from the extract fractionation column. The desorbent recycle stream, taken from the bottom of the extract column, is depleted of $C_9$ aromatic hydrocarbons.

DETAILED DESCRIPTION OF THE INVENTION

A well-known separation process for recovering para-xylene from a mixture of xylene isomers utilizing zeolitic selective adsorbents and a higher boiling desorbent, a countercurrent continuous simulated moving bed process, such as disclosed in Broughton U.S. Pat. No. 2,985,589, is preferred in the practice of the invention.

In the FIGURE, showing the flow scheme of the present invention, the separation unit 1 can be a column containing a number of separate beds of an adsorbent, selective for p-xylene, each having inlet and outlet means. The inlet and outlet means are connected by conduits to valve means, such as a rotary valve described in Carson et al U.S. Pat. No. 3,040,777 or Liebman et al U.S. Pat. No. 3,422,848, regulated by control means to direct feed and desorbent streams to the appropriate beds and withdrawing extract and raffinate output streams from the appropriate beds. Bed movement is simulated by periodically advancing the actual points of liquid addition and withdrawal to respective points in the next bed in a direction so that the apparent movement of adsorbent is opposite the direction of the fluid flow in the column. That is, each inlet and outlet means is shifted by one bed in the same direction as fluid flow. Fluid flow in column 1 is downwardly. Operational zones in the adsorbent column are defined by the position of the input and output streams as follows: adsorption zone I is the adsorbent between the feed inlet and raffinate outlet; purification zone II is the adsorbent between the feed inlet and the extract outlet and is located immediately upstream of zone I; desorption zone III is the adsorbent between the extract outlet and the desorbent inlet and is located directly upstream of zone II. A buffer zone IV is optional, but where used is the adsorbent between the desorbent inlet and the raffinate outlet. Although not shown in the drawing, the top and bottom of the column are interconnected for continuous liquid flow in the column and pump means may be installed in the interconnection to ensure continuous flow in the desired direction.

Adsorbents which may be used in the process are crystalline aluminosilicates, e.g., X or Y zeolites containing Group IA or IIA metal ions at exchangeable cation sites. The preferred exchange ions are barium, potassium or a mixture thereof. Particularly preferred adsorbents are barium-exchanged X or potassium-exchanged Y zeolites. Others which are selective for the p-xylene isomer are also suitable for use in the invention.

Feed is directed into the column 1 through input line 2. The feed may be prefractionated to remove high boiling components, such as $C_{10}$ or higher aromatics in a simple, low cost column, not shown. Although feeds containing as much as 25% (wt.) $C_9$ aromatics may be handled by this process, it is more economical to reduce $C_9$ aromatics in the feed to separation column 1 in a prefractionation column (not shown) to 5% or less, preferably about 2–5% (wt.). Feeds containing less than about 0.1% (wt.) $C_9$ aromatic hydrocarbons do not present a problem of buildup and therefore feeds having at least about 0.1% (wt.) $C_9$ aromatics are contemplated for use in this process. The greatest need, in terms of economic benefit, for this process is in the purification of feedstreams containing substantial amounts of $C_9$ aromatic hydrocarbons, e.g., 2% (wt.) or greater. Suitable feed materials for the process include crystallizer mother liquors, reformates and isomerates containing a mixture of $C_8$ isomers from which it is desired to separate highly pure p-xylene.

Desorbent is directed into the column 1 through input line 3. The desorbents are heavy desorbents, i.e., have a boiling point greater than the $C_9$ aromatics, making it possible to separate the $C_9$ aromatics from the desorbent by simple fractionation and avoid building up $C_9$ aromatic hydrocarbons in the recycled desorbent stream. In the preferred isothermal, isobaric, liquid-phase operation of the process of this invention, when the feed material to the separation process contains substantial amounts of $C_9$ aromatics, the preferred desorbent materials are diethyltoluene isomers and mixtures thereof, tetralin and alkyl or dialkyl derivatives of tetralin and mixtures thereof. The desorbent may also be diluted with a normal paraffin, e.g., n-heptane, to modify the desorbent strength.

The preferred diethyltoluenes contain at least about 40% (wt.) of one or more of the following isomers: 2,3-diethyltoluene (DET), 2,5-DET and 2,6-DET.

Suitable alkyl-substituted derivatives of tetralin include methyl tetralin, ethyl tetralin, propyl tetralin, isopropyltetralin, etc. Suitable dialkyl-substituted derivatives of tetralin include methyl ethyl tetralin, dimethyl tetralin, diethyltetralin, etc. Mixtures of tetralin with one or more of these derivatives, as well as mixtures of these derivatives also may be used with good results.

All position isomers and mixtures are intended to be included when diethyltoluene or any tetralin derivative is referred to herein.

Adsorption conditions will include a temperature range of from about 20° to about 250° C. with about 60° to about 200° C. being more preferred and a pressure just sufficient to maintain liquid phase, which may be from about atmospheric to 600 psig. Desorption conditions will include the same range of temperatures and pressure as used for adsorption conditions.

A raffinate stream 4, comprising the least strongly adsorbed components, ethylbenzene and o- and m-xylene, most of the $C_9$ aromatics, except p-ethyltoluene, and desorbent, is withdrawn from the column 1 at the downstream end of zone I and is directed to a raffinate fractionation column 5.

An extract stream 6, comprising the most strongly adsorbed feed components, p-xylene, toluene, if present, and p-ethyltoluene, and desorbent, is withdrawn from column 1 at the downstream end of zone III and is directed to an extract fractionation column 7. In the fractionation column 7, the extract stream is split into an extract overhead stream 8, comprising p-xylene and any lighter fractions from the feed that were as strongly adsorbed as the p-xylene, for example, toluene and an extract bottoms stream 9 comprising mainly desorbent.

In accordance with the invention, a sidecut stream 10, containing substantially all the $C_9$ aromatics in the extract and a minor amount of desorbent, i.e., about 10 to 20% (wt.) of the desorbent fed to the extract column, is removed from an intermediate tray and introduced into raffinate column 5. Sidecut stream 10 is preferably introduced at a tray below the raffinate feed tray as shown in the FIGURE, but may also be combined with the raffinate (not shown) prior to being introduced into the raffinate column 5. In this way, with little investment, strongly adsorbed $C_9$ aromatics, e.g., ethyltoluene, are separated from the desorbent recycle stream 9, so that $C_9$ aromatics are not recycled back into the separation unit where they may build up and adversely affect the efficiency of the separation. A fractionation column to remove $C_9$ aromatics from the extract desorbent recycle stream is eliminated and furthermore, the $C_9$ aromatics in the sidecut stream directed to the raffinate column 5 contains only 10 to 20% of the desorbent fed to the extract column, thereby reducing the capacity and energy requirements of the raffinate column compared to a drag stream from an extract bottoms stream which contains the same amount of desorbent as the desorbent recycle stream.

In many cases, the feed is prefractionated to remove light fractions, such as toluene and benzene, and therefore the extract overhead stream 8 will contain substantially only p-xylene product at 99% purity or higher. If lighter components remain, however, they may be separated from the p-xylene product by a simple fractionation in a xylene finishing column 11 (XFC) into a light fraction stream 12 and extract product stream 13.

Prior to our invention, an extract bottom stream, containing desorbent and $C_9$ aromatics, was taken from the extract column, but the $C_9$ aromatics would have to be removed from the desorbent, before the desorbent is returned to the adsorbent column 1 in order to avoid the buildup of $C_9$ aromatics in the adsorbent column. Since additional $C_9$ aromatics are brought into the system in the feed, if the $C_9$ aromatics are not removed from the system, they will gradually build up in the adsorbent column, effectively removing a greater and greater portion of the adsorbent capacity. Thus, $C_9$ aromatics were removed from the extract column bottoms stream by fractionation. It had also been suggested that the fractionation column could be eliminated, thereby reducing costs, while lessening the impact of the foregoing problem of $C_9$ aromatic buildup, by directing at least a portion of the extract bottoms stream, i.e., a so-called "drag stream", to the raffinate fractionation column where $C_9$ aromatics could be removed overhead with the raffinate components. In the present invention, all the $C_9$ aromatics are eliminated from the desorbent recycle stream, without the need for separate fractionation equipment. Moreover, the increases in the raffinate column size and energy requirements are considerably less overall than either of the aforementioned prior $C_9$ aromatics separation schemes. Therefore, the present scheme is cost advantageous as well as more efficient.

In fractionation column 5, raffinate materials, o- and m-xylene and ethylbenzene and most of the $C_9$ aromatics, including p-ethyltoluene from sidecut stream 10 are recovered in the overhead 14 and may be directed to an isomerization process along with the light overhead 12 from column 11 to be converted to additional p-xylene-rich feed for the separation process. Desorbent is removed from the bottom of the fractionation column 5 in raffinate bottoms stream 15 and recycled back into the separation column 1 via line 3. A small portion of the desorbent recycle stream may be removed from the system via line 16 and periodically treated, e.g., by fractionation to remove any trace impurities, such as high molecular weight aromatics or $C_{12}^+$ tetralins which may have built up in the desorbent.

EXAMPLE

This example is a computer simulation to illustrate the preferred embodiment of the process shown in FIG. 1 utilizing a continuous simulated moving bed countercurrent type of operation in which a portion of the extract column bottoms is directed to the raffinate fractionation column and the remainder is recycled to the adsorption separation unit 1. The computer simulation makes engineering calculations based on actual experience in operating these components in similar commercial processing units under the selected conditions for the present process. The processing units for the simulation are arranged as in the FIGURE and will be referred to using the reference numbers appearing in the drawing. A reformate feed stream having the composition of Table 1 is fed to the separation unit 1 via line 2. Desorbent, tetralin, is fed into the column in desorbent stream 3. The separation unit 1 comprises 24 beds filled with BaX zeolite. The raffinate is withdrawn from the separation unit 1 through line 4 and directed to the raffinate fractionation column 5 for fractionation into overhead stream 14 containing o- and m-xylene, ethylbenzene, $C_9$ aromatics including p-ethyltoluene and bottoms stream 17 comprising desorbent tetralin. The extract, containing p-xylene, p-ethyltoluene, toluene and desorbent, is withdrawn from the separation unit 1 through line 6 and directed to the extract column 7 for fractionation into overhead stream 8, comprising para-xylene of 95.0% purity, bottoms stream 9 comprising desorbent and sidecut stream 10 containing p-ethyltoluene and desorbent. Extract bottoms stream 9 is recycled to the separations unit, combined with makeup desorbent and raffinate column bottoms via lines 9, 15 and 3. Sidecut stream 10 containing p-ethyltoluene, diluted with about 15% (wt.) of the desorbent fed to the extract column, is sent to raffinate column 5.

The extract column overhead stream 8, containing toluene and p-xylene, is directed to xylene fractionation column 11 where toluene is removed in overhead line 12 and p-xylene is recovered from line 13 at 99.8% purity. Para-xylene recovery is 97.0%.

The operating conditions for the separation unit are:

Temperature: 350° F. (177° C.)
Pressure: 125.

The material balance for the process is based on a feed rate of 362,579 lb per hr and a desorbent rate of 453,936 lb per hr. Also shown in Table 2 for comparison is an example, also a simulation, based on the prior proposal mentioned above where a 50% (wt.) drag stream, taken from the extract column bottoms, is directed to the raffinate column, instead of the sidecut of the present invention. In both cases, $C_9$ aromatics are removed from the system in the raffinate column overhead, but the present invention avoids recycling any $C_9$ aromatics to the separation unit and also reduces the amount of desorbent in the $C_9$ aromatic stream, from the extract column, which must be separated in the raffinate column. Both effects result in reduced capital and process energy costs. Para-xylene recovery is 97.0%.

TABLE 1

| Component | Feed Composition | |
|---|---|---|
| | lbs/hr | wt. % |
| n-$C_8$ | 3,833 | 1.06 |
| n-$C_9$ | 302 | 0.08 |
| n-$C_{10}$ | 83 | 0.02 |
| Ethylcyclohexane | 15,330 | 4.23 |
| Toluene | 3,836 | 1.06 |
| p-Xylene (p-X) | 68,872 | 19.00 |
| o-Xylene (o-X) | 65,448 | 18.05 |
| m-Xylene (m-X) | 163,186 | 45.01 |
| Ethylbenzene | 34,425 | 9.49 |
| $C_9$ Aromatics ($C_9$ A) | | |
| n-propyl benzene | 381 | 0.11 |
| isopropyl benzene | 500 | 0.14 |
| o-ethyltoluene | 396 | 0.11 |
| m-ethyltoluene | 1,741 | 0.48 |
| p-ethyltoluene (p-ET) | 866 | 0.24 |
| 1,2,3-Trimethylbenzene | 55 | 0.02 |
| 1,2,4-Trimethylbenzene | 2,018 | 0.56 |
| 1,3,5-Trimethylbenzene | 1,307 | 0.36 |
| TOTAL | 362,579 | 100.00 |

TABLE 2

| Stream and Component | PRESENT INVENTION Ext. Col Sidecut to Raff. Col. | | PRIOR PROCESS | |
|---|---|---|---|---|
| | Lbs/hr | wt. % | Lbs/hr | wt. % |
| | | | 50% Ext. Bottoms to Raff. Col. | |
| Extract | | | | |
| Toluene | 2,302 | 1.01 | 2,302 | 1.01 |
| $C_8$ A: p-X | 66,806 | 29.35 | 66,806 | 29.27 |
| Other (o-X,m-x,Ethylbenzene) | 134 | 0.06 | 134 | 0.06 |
| $C_9$ A: p-ET | 866 | 0.38 | 1,496 | 0.66 |
| Tetralin | 157,487 | 69.20 | 157,487 | 69.01 |
| Total | 227,595 | 100.00 | 228,225 | 100.01 |
| Extract Column Overhead | | | | |
| Toluene | 2,302 | 3.33 | 2,302 | 3.32 |
| $C_8$ A: p-X | 66,737 | 96.48 | 66,806 | 96.48 |
| Other | 133 | 0.19 | 134 | 0.19 |
| Total | 69,172 | 100.00 | 69,242 | 99.99 |
| Extract Bottoms to Recycle Desorbent | | | | |
| $C_9$ A: p-ET | 0 | 0.00 | 748 | 0.94 |
| Tetralin | 134,658 | 100.00 | 78,743 | 99.06 |
| Total | 134,658 | 100.00 | 79,491 | 100.00 |
| | | | Extract Bottoms to Raffinate Column | |
| Sidecut Stream to Raffinate | | | | |
| $C_8$ A: p-X | 69 | 0.29 | 0 | 0.00 |
| Other | 1 | 0.00 | 0 | 0.00 |
| $C_9$ A: p-ET | 866 | 3.64 | 748 | 0.94 |
| Tetralin | 22,829 | 96.06 | 78,744 | 99.06 |

TABLE 2-continued

| Stream and Component | PRESENT INVENTION Ext. Col Sidecut to Raff. Col. | | PRIOR PROCESS | |
|---|---|---|---|---|
| | Lbs/hr | wt. % | Lbs/hr | wt. % |
| Total | 23,765 | 100.00 | 79,492 | 100.00 |
| | | | 50% Ext. Bottoms to Raff. Col. | |
| Raffinate | | | | |
| Sats | 19,548 | 3.32 | 19,548 | 3.32 |
| Toluene | 1,534 | 0.26 | 1,534 | 0.26 |
| $C_8$ A: p-X | 2,066 | 0.35 | 2,066 | 0.35 |
| Other | 262,925 | 44.65 | 262,925 | 44.64 |
| $C_9$ A: p-ET | 0 | 0.00 | 118 | 0.02 |
| Other | 6,398 | 1.09 | 6,398 | 1.09 |
| Tetralin | 296,449 | 50.34 | 296,449 | 50.33 |
| Total | 588,920 | 100.01 | 589,038 | 100.01 |
| Raffinate Column Overhead | | | | |
| Sats | 19,548 | 6.66 | 19,548 | 6.66 |
| Toluene | 1,534 | 0.52 | 1,534 | 0.52 |
| $C_8$ A: p-X | 2,135 | 0.73 | 2,066 | 0.70 |
| Other | 262,926 | 89.61 | 262,925 | 89.63 |
| $C_9$ A: p-ET | 866 | 0.30 | 866 | 0.30 |
| Other | 6,398 | 2.18 | 6,398 | 2.18 |
| Total | 293,407 | 99.99 | 293,337 | 99.99 |
| Raffinate Bottoms Recycle Desorbent | | | | |
| Tetralin | 319,278 | 100.00 | 375,193 | 100.00 |
| Total | 319,278 | 100.00 | 375,193 | 100.00 |
| Total to Recycle Desorbent | | | | |
| $C_9$ A: p-ET | 0 | 0.00 | 748 | 0.16 |
| Tetralin | 435,936 | 100.00 | 453,936 | 99.84 |
| Total | 435,936 | 100.00 | 454,684 | 100.00 |

What is claimed is:

1. A process for the production and recovery of para-xylene from an aromatic feed stream comprising $C_8$ aromatic hydrocarbons and up to about 25% (wt.) $C_9$ aromatic hydrocarbons comprising the steps of:

(a) contacting said feed stream with an adsorbent selective for para-xylene and relatively less selective for the other $C_8$ aromatic hydrocarbons in a separation zone;

(b) removing a raffinate stream comprising the less selectively adsorbed feed components and desorbent from contact with said adsorbent;

(c) contacting said adsorbent with a heavy desorbent having 10 to 12 carbon atoms, at desorption conditions, to effect the removal of an extract stream comprising para-xylene, $C_9$ aromatic hydrocarbons and desorbent;

(d) fractionating said extract stream in an extract fractionator to produce an extract overhead stream comprising para-xylene, a sidecut stream comprising substantially all of said $C_9$ aromatics in said extract and a minor amount of the desorbent in said extract stream and an extract bottoms stream comprising a major amount of the desorbent in said extract stream;

(e) fractionating said raffinate stream and said sidecut stream in a raffinate fractionator to produce a raffinate overhead stream comprising said less selectively adsorbed $C_8$ isomers and $C_9$ aromatics and a bottoms stream comprising desorbent; and (f) recovering para-xylene from said extract overhead stream.

2. The process of claim 1 wherein said heavy desorbent comprises diethyltoluene, tetralin or tetralin derivatives or mixtures thereof.

3. The process of claim 1 where said less selectively adsorbed $C_8$ isomers and $C_9$ aromatics are recovered from said raffinate overhead stream.

4. The process of claim 1 wherein said extract bottoms stream is recycled to said separation zone.

5. The process of claim 1 wherein said extract bottoms stream and said raffinate bottoms stream are recycled to step (c).

6. The process of claim 1 wherein said feed stream contains from about 2 to about 5% (wt.) $C_9$ aromatic hydrocarbons.

7. The process of claim 1 wherein said less selectively adsorbed feed components comprise ethylbenzene, m-xylene, o-xylene and $C_9$ aromatic hydrocarbons, except para-ethyltoluene.

8. The process of claim 1 wherein said sidecut stream is combined with said raffinate stream before entering said raffinate column.

9. The process of claim 1 wherein said sidecut stream enters said raffinate column at a tray below the entry tray of said raffinate stream.

* * * * *